US00PP33865P2

(12) United States Plant Patent
ter Laak

(10) Patent No.: US PP33,865 P2
(45) Date of Patent: Jan. 11, 2022

(54) ***BEGONIA* PLANT NAMED 'BETESORANG'**

(50) Latin Name: ***Begonia boliviensis* X *Begonia tuberhyrida***
Varietal Denomination: BeTesorang

(71) Applicant: H. M. TESSELAAR FREESIA B.V., Heerhugowaard (NL)

(72) Inventor: Wendela Antoinette ter Laak, Zandvoort (NL)

(73) Assignee: H.M. TESSELAAR FREESIA B.V., Heerhugowaard (NL)

( * ) Notice: Subject to any disclaimer, the term of this patent is extended or adjusted under 35 U.S.C. 154(b) by 0 days.

(21) Appl. No.: 17/334,438

(22) Filed: May 28, 2021

(51) Int. Cl.
*A01H 5/02* (2018.01)
*A01H 6/18* (2018.01)

(52) U.S. Cl.
USPC ..... Plt./347

(58) Field of Classification Search
USPC ..... Plt./344, 347
See application file for complete search history.

*Primary Examiner* — Susan McCormick Ewoldt
(74) *Attorney, Agent, or Firm* — C. Anne Whealy

(57) ABSTRACT

A new and distinct cultivar of *Begonia* plant named 'BeTesorang', characterized by its uniform, upright to broadly outwardly spreading plant habit; freely branching habit; dark green-colored leaves; freely flowering habit; and single-type female and semi-double male flowers that are bright orange in color.

1 Drawing Sheet

Botanical designation: *Begonia boliviensis* X *Begonia tuberhyrida.*

Cultivar denomination: 'BeTesorang'.

Inventor/Applicant claims priority to a European Community Plant Breeders' Rights application filed for the instant plant filed on Jun. 3, 2020, application number 2020/1216. No accessibility to one of ordinary skill in the art could have been derived from the printed Plant Breeder's Rights documents.

STATEMENT REGARDING PRIOR DISCLOSURES BY THE INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia boliviensis* X *Begonia tuberhybrida*, commonly referred to as a Hybrid Tuberous *Begonia* and hereinafter referred to by the name 'BeTesorang'.

The new *Begonia* plant is a product of a planned breeding program conducted by the Inventor in Heerhugowaard, The Netherlands. The objective of the breeding program is to create new vigorous and strong *Begonia* plants with numerous attractive flowers and good garden performance.

The new *Begonia* plant originated from a cross-pollination on May 30, 2014 of a proprietary selection of *Begonia boliviensis* X *Begonia tuberhybrida* identified as code number 13-551-07, not patented, as the female, or seed, parent with a proprietary selection of *Begonia boliviensis*X *Begonia tuberhybrida* identified as code number 13-489-14, not patented, as the male, or pollen, parent. The new *Begonia* plant was discovered and selected as a single flowering plant from within the progeny of the stated cross-pollination in a controlled greenhouse environment in Heerhugowaard, The Netherlands on Nov. 21, 2014.

Asexual reproduction of the new *Begonia* plant by vegetative terminal cuttings in a controlled greenhouse environment in Heerhugowaard, The Netherlands, since Dec. 14, 2014 has shown that the unique features of this new *Begonia* plant are stable and reproduced true to type in successive generations of asexual reproduction.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BeTesorang'. These characteristics in combination distinguish 'BeTesorang' as a new and distinct *Begonia* plant:

1. Uniform, upright to broadly outwardly spreading plant habit.
2. Freely branching habit.
3. Dark green-colored leaves.
4. Freely flowering habit.
5. Single-type female and male flowers that are bright orange in color.

Plants of the new *Begonia* can be compared to plants of the female parent selection. Plants of the new *Begonia* differ primarily from plants of the female parent selection in the following characteristics:

1. Plants of the new *Begonia* are more freely branching than plants of the female parent selection.
2. Flower tepals of plants of the new *Begonia* are straight whereas flower tepals of plants of the female parent selection are reflexed.

Plants of the new *Begonia* can be compared to plants of the male parent selection. Plants of the new *Begonia* differ primarily from plants of the male parent selection in the following characteristics:

1. Plants of the new *Begonia* are more freely branching than plants of the male parent selection.
2. Plants of the new *Begonia* have larger and darker green leaves than plants of the male parent selection.
3. Flowers of plants of the new *Begonia* are bright orange in color whereas flowers of plants of the male parent selection are orange and white in color.

Plants of the new *Begonia* can be compared to plants of the *Begonia pendula*X *Begonia boliviensis* 'Encanto Orange', disclosed in U.S. Plant Pat. No. 20,898. In side-by-side comparisons, plants of the new *Begonia* differ from plants of 'Encanto Orange' in the following characteristics:

1. Plants of the new *Begonia* are more rounded than plants of 'Encanto Orange'.
2. Plants of the new *Begonia* have darker green-colored leaves than plants of 'Encanto Orange'.
3. Flowers of plants of the new *Begonia* have shorter tepals than flowers of plants of 'Encanto Orange'.

Plants of the new *Begonia* can also be compared to plants of the *Begonia boliviensis* 'Bonfire', disclosed in U.S. Plant Pat. No. 15,108. In side-by-side comparisons, plants of the new *Begonia* differ from plants of 'Bonfire' in the following characteristics:

1. Plants of the new *Begonia* have larger and darker green-colored leaves than plants of 'Bonfire'.
2. Plants of the new *Begonia* have larger flowers than plants of 'Bonfire'.
3. Flowers of plants of the new *Begonia* have shorter tepals than flowers of plants of 'Bonfire'.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph is a side perspective view of a typical flowering plant of 'BeTesorang' grown in a container.

DETAILED BOTANICAL DESCRIPTION

Plants used for the aforementioned photograph and following observations and measurements were grown in 13-cm containers during the winter and early spring in a glass-covered greenhouse in Venhuizen, The Netherlands. Plants were 16 weeks old when the photograph and the description were taken. In the following description, color references are made to The Royal Horticultural Society Colour Chart, 2015 Edition, except where general terms of ordinary dictionary significance are used.

Botanical classification: *Begonia boliviensis* X *Begonia tuberhybrida* 'BeTesorang'.

Parentage:

*Female, or seed, parent.*—Proprietary selection of *Begonia boliviensis*X *Begonia tuberhybrida* identified as code number 13-551-07, not patented.

*Male, or pollen, parent.*—Proprietary selection of *Begonia boliviensis*X *Begonia tuberhybrida* identified as code number 13-489-14, not patented.

Propagation:

*Type.*—By vegetative tip cuttings.

*Time to initiate roots, summer.*—About one week.

*Time to produce a rooted young plant, summer.*—About three to four weeks.

*Root description.*—Fine, fibrous; typically whitish in color, actual color of the roots is dependent on substrate composition, water quality, fertilizer type and formulation, substrate temperature and physiological age of roots; plants of the new *Begonia* have not been observed to form tubers.

*Rooting habit.*—Freely branching; dense.

Plant description:

*Plant and growth habit.*—Uniform, upright to broadly outwardly spreading plant habit; plant shape roughly flattened globular to spreading; freely branching habit with about seven basal branches each with about two to three lateral branches developing per plant; moderately vigorous to vigorous growth habit and moderate growth rate.

*Plant height, soil level to top of foliar plane.*—About 20.8 cm.

*Plant height, soil level to top of floral plane.*—About 19.5 cm.

*Plant width.*—About 51.1 cm.

*Lateral branch description.*—Length: About 17.5 cm. Diameter: About 7 mm. Internode length: About 2.9 cm. Strength: Moderately weak, bending with the weight of the leaves and flowers. Aspect: Ranging from about 40° to about 80° from vertical. Texture and luster: Moderately pubescent; moderately glossy. Color, developing: Close to 199A. Color, developed: Close to N199A; at the internodes, close to N199A slightly tinged with close to 183A.

*Leaf description.*—Arrangement: Alternate, distichous; simple. Length: About 12.9 cm. Width: About 4.8 cm. Shape: Lanceolate. Apex: Narrowly acute. Base: Broadly oblique; lobes not imbricate. Margin: Dentate to serrate and doubly dentate to serrate. Texture and luster, upper surface: Smooth, glabrous; slightly velvety; slightly glossy. Texture and luster, lower surface: Smooth and mostly glabrous with sparse pubescence along midvein; slightly velvety; slightly glossy. Venation pattern: Pinnate. Color: Developing leaves, upper surface: A blend of close to 187A and 200B. Developing leaves, lower surface: A blend of close to N186C and 187A. Fully expanded leaves, upper surface: Darker than a blend of close to N189A and 203A; venation, close to 145A and towards the petiole, close to N144A. Fully expanded leaves, lower surface: Close to 183B; venation, close to 152A. Petioles: Length: About 3.1 cm. Diameter: About 3 mm. Texture and luster, upper and lower surfaces: Sparsely pubescent; moderately glossy. Strength: Low. Color, upper surface: Close to 175A; towards the leaf attachment, close to 185A. Color, lower surface: Close to 178B. Stipules: Quantity per leaf: Two at the base of each leaf. Length: About 9 mm. Width: About 5 mm. Shape: Deltoid to ovate. Apex: Acute. Base: Broadly cuneate. Margins: Entire, ciliate. Color, upper and lower surfaces: Close to 181C; venation, close to 183C.

Flower description:

*Flowering habit.*—Rotate female and male flowers are single-types; flowers arranged in simple axillary cymes; freely flowering habit with about three flowers per cyme and about 280 flowers developing per plant during the flowering season; flowers face outwardly to nodding or drooping.

*Fragrance.*—None detected.

*Natural flowering season.*—Long flowering period; plants flower freely and continuously from spring into the autumn in The Netherlands; plants begin flowering about six weeks after pinching.

*Flower longevity.*—Individual flowers last about ten days on the plant; flowers not persistent.

*Inflorescence height (including peduncle).*—About 14.9 cm.

*Inflorescence diameter.*—About 11.8 cm.

*Flower buds, female flowers.*—Length: About 2.6 cm. Diameter, flattened: About 6 mm to 7 mm. Shape: Ovate; flattened. Texture and luster: Smooth, glabrous; velvety; matte. Color: Close to 32A.

*Flower buds, male flowers.*—Length: About 3.5 cm. Diameter, flattened: About 9 mm to 23 mm. Shape: Roughly obovate; flattened. Texture and luster: Smooth, glabrous; velvety; matte. Color: Close to 32A.

*Female flowers.*—Size: About 6.5 cm by 6.5 cm. Depth: About 3.5 cm. Tepals: Quantity per flower and arrangement: Five in two whorls; inner whorl with three tepals and outer whorl with two tepals. Length, inner tepals: About 3.4 cm. Length, outer tepals: About 3.5 cm. Width, inner tepals: About 1.5 cm. Width, outer tepals: About 2.1 cm. Shape, inner tepals: Narrowly obovate to oblanceolate. Shape, outer tepals: Ovate to narrowly ovate. Apex, inner tepals: Obtuse. Apex, outer tepals: Acute. Base, inner and outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; moderately velvety; mostly matte with the base, slightly glossy. Color, inner and outer tepals: When opening and fully opened, upper surface: Close to 33B; venation, close to 35A; color becoming closer to 30A with subsequent development. When opening and fully opened, lower surface: Close to 32A; venation, close to 32A; color does not change with subsequent development. Tepaloids: None observed on female flowers.

*Male flowers.*—Size: About 6.9 cm by 6.9 cm. Depth: About 3.9 cm. Tepals: Quantity per flower and arrangement: Four in two whorls; inner whorl with two tepals and outer whorl with two tepals. Length, inner tepals: About 4.4 cm. Length, outer tepals: About 4.7 cm. Width, inner tepals: About 1.5 cm. Width, outer tepals: About 2.9 cm. Shape, inner tepals: Narrowly oblong. Shape, outer tepals: Narrowly ovate to narrowly elliptic. Apex, inner tepals: Rounded. Apex, outer tepals: Acute. Base, inner tepals: Attenuate. Base, outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; moderately velvety; mostly matte with the base, moderately glossy. Color, inner and outer tepals: When opening and fully opened, upper surface: Close to 33B; venation, close to 35A; color becoming closer to 30A with subsequent development. When opening and fully opened, lower surface: Close to 32A; venation, close to 35A; color does not change with subsequent development. Tepaloids: Quantity per flower and arrangement: About two at the center of the flower, opposite. Length: About 1.9 cm. Width: About 3 mm. Shape: Lanceolate. Apex: Bluntly acute. Base: Narrowly attenuate. Margin: Entire; not undulate. Texture and luster, upper and lower surfaces: Smooth, glabrous; slightly velvety; matte. Color: When opening and fully opened, upper surface: Close to 29B; towards the margins, close to 29A and towards the apex, close to 32A; venation, similar to lamina colors; color does not change with subsequent development. When opening and fully opened, lower surface: Close to 29B; towards the margins, close to 29A and towards the apex, close to 32A; venation, similar to lamina colors; color does not change with subsequent development.

*Peduncles.*—Length: About 8.9 cm. Diameter: About 3 mm. Angle: About 50° from lateral branch axis. Strength: Moderately weak; flexible and bending with the weight of the flowers. Texture and luster: Smooth, glabrous; moderately glossy. Color, upper surface: Close to 172A. Color, lower surface: Close to 174A.

*Pedicels, female flowers.*—Length: About 3.1 cm. Diameter: About 2 mm. Angle: About 45° from the peduncle axis. Strength: Moderately weak; flexible, bending with the weight of the flowers. Texture and luster: Sparsely pubescent; glossy. Color, upper surface: Close to 34B. Color, lower surface: Close to 31B.

*Pedicels, male flowers.*—Length: About 3 cm. Diameter: About 2.5 mm. Angle: Mostly upright. Strength: Moderately weak; flexible, bending with the weight of the flowers. Texture and luster: Smooth, glabrous; glossy. Color, upper surface: Close to 34B. Color, lower surface: Close to 31B.

*Flower bracts.*—Quantity per flower and arrangement: Two, at the top of the peduncles. Length: About 1.2 cm. Width: About 1.6 cm. Shape: Reniform. Apex: Rounded. Base: Broadly cuneate. Margin: Entire; ciliate. Texture and luster, upper and lower surfaces: Smooth, glabrous; slightly glossy. Color, upper and lower surfaces: Close to 173B tinged with close to 195B and towards the margins, close to 34B.

*Reproductive organs.*—Androecium: Present only on male flowers. Stamen quantity per flower: About 70. Filament length: About 4 mm. Filament color: Close to 11A. Anther size: About 1 mm by 1.5 mm. Anther shape: Obovate. Anther color: Close to 13A. Amount of pollen: Moderate. Pollen color: Close to 4D.

Gynoecium: Present only on female flowers. Quantity per flower: About three. Pistil length: About 6 mm. Stigma diameter: About 5 mm. Stigma shape: Cleft. Stigma color: Close to 14A. Style length: About 5 mm. Style color: Close to 25A. Ovary color: Close to 145A tinged with close to N170B and at the apex, close to 171A. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BeTesorang' as illustrated and described.

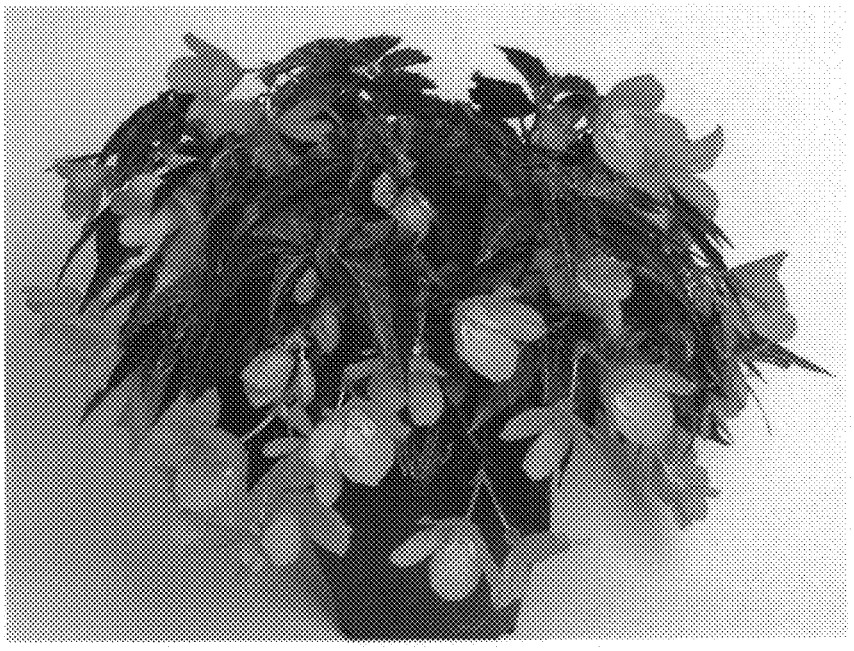

* * * * *